(12) United States Patent
Noe' et al.

(10) Patent No.: US 6,891,040 B2
(45) Date of Patent: May 10, 2005

(54) HIGH YIELDS, HIGH PURITY MELAMINE MANUFACTURING PROCESS

(75) Inventors: Sergio Noe', Milan (IT); Massimo Parmegiani, Varese (IT); Giovanni Morello, Milan (IT)

(73) Assignee: Eurotecnica Group S.A., Basel (CH)

( * ) Notice: Subject to any disclaimer, the term of this patent is extended or adjusted under 35 U.S.C. 154(b) by 0 days.

(21) Appl. No.: 10/168,440

(22) PCT Filed: Dec. 7, 2000

(86) PCT No.: PCT/IT00/00508

§ 371 (c)(1),
(2), (4) Date: Oct. 17, 2002

(87) PCT Pub. No.: WO01/46159

PCT Pub. Date: Jun. 28, 2001

(65) Prior Publication Data

US 2003/0100758 A1 May 29, 2003

(30) Foreign Application Priority Data

Dec. 22, 1999 (IT) ......................... MI99A2684

(51) Int. Cl.$^7$ ..................... C07D 251/60; C07D 251/62
(52) U.S. Cl. ..................... 544/201; 544/203
(58) Field of Search ................. 544/203, 201

(56) References Cited

U.S. PATENT DOCUMENTS 2,647,119 A * 7/1953 Haworth et al. ............ 544/203
2,863,869 A * 12/1958 Elmer et al. ................ 544/203
3,250,773 A * 5/1966 Christoffel et al. ......... 544/203
3,423,411 A * 1/1969 Dakli et al. ................. 544/203
3,496,176 A * 2/1970 Kennedy et al. ............ 544/203

FOREIGN PATENT DOCUMENTS

EP          091 174        10/1983
WO          95/06042       3/1995

OTHER PUBLICATIONS

DOE?EM–0370–Innovative Technology Summary Report: Cros Flow Filtratiom 1998.*
Bucher Cross Flow Filteration.*

* cited by examiner

Primary Examiner—Venkataraman Balasubramanian
(74) Attorney, Agent, or Firm—Pauley Petersen & Erickson

(57) ABSTRACT

The process to recover both melamine and oxyaminotriazines (OAT) from the mother liquors of melamine crystallisation comprising the following steps: a) addition to a melamine and OAT containing aqueous solution at high temperature of an alkaline agent until the solution pH reach a value equal or higher than 11; b) most of melamine crystallisation by solution cooling; c) separation and recovery of precipitated melamine; d) acidification of the obtained solution, after precipitated melamine separation, in order to reach a pH of about 7; e) the suspension obtained in d) above after precipitated melamine recovery, is subject to filtration according to tangential filtration technique obtaining a clear permeate which contains as a solution all melamine which did not precipitate in step b) and a retentate comprising of OAT dispersion; f) OAT deprived mother liquors from e) are recycled to row melamine solution preparation step; in such a way almost the total amount of melamine, which did not precipitate in step b), is recovered; g) OAT are recovered from step e) retentate by using any conventional separation technics.

17 Claims, 3 Drawing Sheets

HIGH YIELDS, HIGH PURITY MELAMINE MANUFACTURING PROCESS

TECHNICAL FIELD

This invention refers to a high yields high purity melamine manufacturing process starting from urea.

BACKGROUND ART

More particularly, this invention concerns a simple and unexpensive process to separately recover melamine and some important by-products deriving from the melamine synthesis reaction or its subsequent treatments, as well as from solutions or dispersions containing melamine and said by-products formed in the course of melamine purification cycle. In fact, it is known that in almost all melamine processes starting from urea, both catalytic or without catalyst, the raw reaction product is dissolved in water, then submitted to one or more purification steps, finally the product having the requested purity level, is separated from the solution by crystallisation.

During the melamine water solution treatment, temperature is kept at levels higher than 130° C., (preferably 160 to 170° C.) in order to take advantage of the higher melamine solubility and, consequently, minimising the water volume to be handled.

Higher temperatures are not desired because of more water steam entraining in the effluent—so-called off-gas essentially consisting of $NH_3$ and $CO_2$, more equipment corrosions, as well as more hydrolysis melamine losses. The resulting product, consisting of high purity degree melamine (>99.8% grade), is eventually separated from the solution by cooling and subsequent crystallisation at a temperature of 40–50° C. In these conditions most of melamine precipitates in crystalline form and is separated by filtration or centrifugation or any suitable conventional means. Aqueous solution, after high purity melamine separation contains, besides melamine, Oxyaminotriazines (OAT) which include both amelide and ameline having the following formulas:

amelide                ameline

OAT besides being melamine synthesis reaction intermediate products, are also formed in the aqueous solution because of melamine hydrolysis. Therefore OAT are always present in the aqueous solution from which melamine is recovered.

OAT are products much less water soluble than melamine, but its water solubility increases by some orders of magnitude when pH increases, whilst melamine solubility remains practically unchanged within the pH range of 7 to 14.

Such a different behaviour makes possible the crystallisation of melamine alone when a melamine and OAT-containing solution at a pH higher than 7, preferably higher than 11, is cooled.

The high pH value is obtained by adding to the solution an alkaline compound such as ammonia or sodium hydroxide.

The crystallisation mother liquor recovered after the precipitation and separation of melamine contains therefore in a solution the entire starting amount of OAT plus the residual melamine corresponding to the melamine solubility at the crystallisation conditions.

For instance, by operating the crystallisation at 40° C. and a pH higher than 11, the resulting mother liquor contains the following amounts of melamine and OAT:

| melamine | 0.7/1 wt % |
|---|---|
| OAT | 0.3–0.5 wt %. |

In order to obtain a high melamine yield from the manufacturing process it is necessary to recycle to the process the entire amount of such mother liquor or a portion thereof. However before recycling the mother liquor it is necessary to remove OAT, otherwise OAT accumulate in the recycling solution up to the saturation point and then precipitate together with melamine polluting same.

To maintain the cycle equilibrium it is necessary to remove from the mother liquor the same amount of OAT formed both in the reaction zone and in the aqueous solution by melamine hydrolysis.

The above operation is accomplished by acidifying the mother liquor, obtained after melamine crystals removal, with a suitable acid, to the pH value of 7. Typically the acidification agent is $CO_2$ in order to avoid the introduction of any foreign substance in the process fluids.

At pH 7 OAT are practically insoluble in water and therefore they precipitate completely; on the contrary, melamine, due to the fact that its solubility, within the range of pH 7 to 14, is independent on pH, does not precipitates. Therefore, once the OAT are separated, the mother liquor can be partially or totally recycled to the process obtaining the partial or total recovery of the melamine content.

The separation of precipitated OAT is difficult to be carried out due to the colloidal nature of OAT precipitate.

As a matter of fact, OAT suspended in the acidified mother liquor, are hardly separated by settling, even if the operation is carried out in a high velocity centrifugal equipment. Also filtration operations are very difficult and in practice can not be used in that the filtration cake colloidal nature is such that filtration surface is rapidly blocked. The only system allowing the separation is the filtration assisted by filtration aids like, for instance infusorial earth (dicalite or similar products). Also in this case, however, filtration is not completely satisfactory and the filter life cycle (including filtration aid loading—filtration—cake removal—washing) typically does not operate for more than 4 hours. In addition OAT are obtained as a mixture with a foreign material (the filtration aid) that makes difficult their separation.

Then it results that the only industrially applicable operation to separate OAT (i.e. filtration in presence of a filtration aid) is very expensive in that:

it requires high investment costs because of operating complexity as well as the required high filtering surface;

it requires much manpower to carry out the filtration cycle which is repeated every 4 hours;

it consumes a big amount of filtration aid (5 to 30 wt % based on the separated OAT)

it allows only a partial melamine recovery, because being an imperfect filtration, it is necessary to purge a substantial amount of filtrate to avoid the OAT accumulation in the water cycle, it recovers an OAT/filtration aid mixed panel, which is practically useless.

Because of the above problems, processes have been studied and operated implying the total decomposition to $CO_2$ and $NH_3$ of the organic products contained in the mother liquor. Said processes, besides of decomposing OAT, they destroy also the melamine (that may be profitably recovered) and consume a significant amount of energy and require large investment costs.

This invention intends to obviate to all the abovementioned drawbacks by means of a process that allows to recover from the melamine crystallisation mother liquor both the residual dissolved melamine and the OAT.

DISCLOSURE OF THE INVENTION

The process according to the present invention comprises the following steps:

a) addition to a melamine and OAT containing aqueous solution at high temperature of an alkaline agent until the solution pH reaches a value equal or higher than 11.

b) Crystallisation of the most part of melamine by cooling the solution resulting from step a).

c) Separation and recovery of the precipitated melamine d) Acidification of the resulting solution (mother liquor), after precipitated melamine separation, in order to reach a pH of about 7 in consequence of which practically all the dissolved OAT are precipitated.

e) The suspension obtained in d) above, is subject to filtration according to tangential filtration technique obtaining a clear permeate which contains as a solution all the melamine not precipitated in step b) and a retentate comprising of OAT dispersion.

f) OAT deprived mother liquor from e) (the permeate) is recycled to the raw melamine solution preparation step; in such a way almost the total amount of melamine, not precipitated in step b), is recovered.

g) OAT are recovered from step e) retentate by using any conventional separation technique.

It has been found that by operating according with the above procedure and utilising the so-called tangential filtration technologies, it is possible to recover more than 94% and up to 96% of mother liquor (containing 0.7 to 1% wt of melamine), leaving in such mother liquor an OAT content lower than 100 ppm, i.e. the content corresponding to OAT solubility at a pH 7 and an operating temperature of about 40 to 50° C.

The temperature of the solution to be additioned of alkaline agent according to step a) is higher than 130° C. and, preferably is 160 to 180° C., while the crystallisation temperature according to step b) is about 40 to 50° C.

Tangential filtration is a filtration technique wherein the suspension to be filtered moves at a high speed along a direction which is parallel to filtrating surface in order to create a suspension turbulence which prevents the filtration cake formation as well as the frequent filter blocking.

While suspension flows at high speed parallel to filtering surface, solute passes through the filtering surface holes because of the pressure difference and is continuously removed.

Filtering surface should be such as to mechanically resist to pressure difference between the retentate compartment (i.e. the suspension concentrating compartment) and permeate compartment (clear filtered solution free from suspended particles); moreover, filtering surface should exhibit a suitable chemical resistance to process fluid and a porous structure such as to prevent the passage of the suspended OAT colloidal micelles and/or crystalline aggregates.

For the specific application of the invention, it has been found that the filtrating surface can be alumina made which is commercially available with a high purity grade. However, other materials satisfying the above requirements can be advantageously used.

Among the materials useful for filtration surface preparation the following can be mentioned: silico-alumina, zirconia, titania, boria, zeolites, thoria and mixture thereof. Filtration surface porosity (i.e. mean diameter of passage pores) should be lower than 5 micrometers, preferably lower than 0.2 micrometers with the range of 20–100 nanometers being the most preferred. A porosity lower than 20 nanometers requires high differential pressures. The differential pressure being the same, allows very low specific filtrate flow and consequently low productivity. Porosity higher than 5 micrometers does not guarantee a good separation.

BRIEF DESCRIPTION OF THE DRAWING

The invention will be better understood and the relevant advantages will be evident from the following description of some application examples given in connection with the enclosed drawings. Description and drawing shall in no way be interpreted as restrictive of the present invention.

DETAILED DESCRIPTION OF PREFERRED EMBODIMENTS

Figure 1:
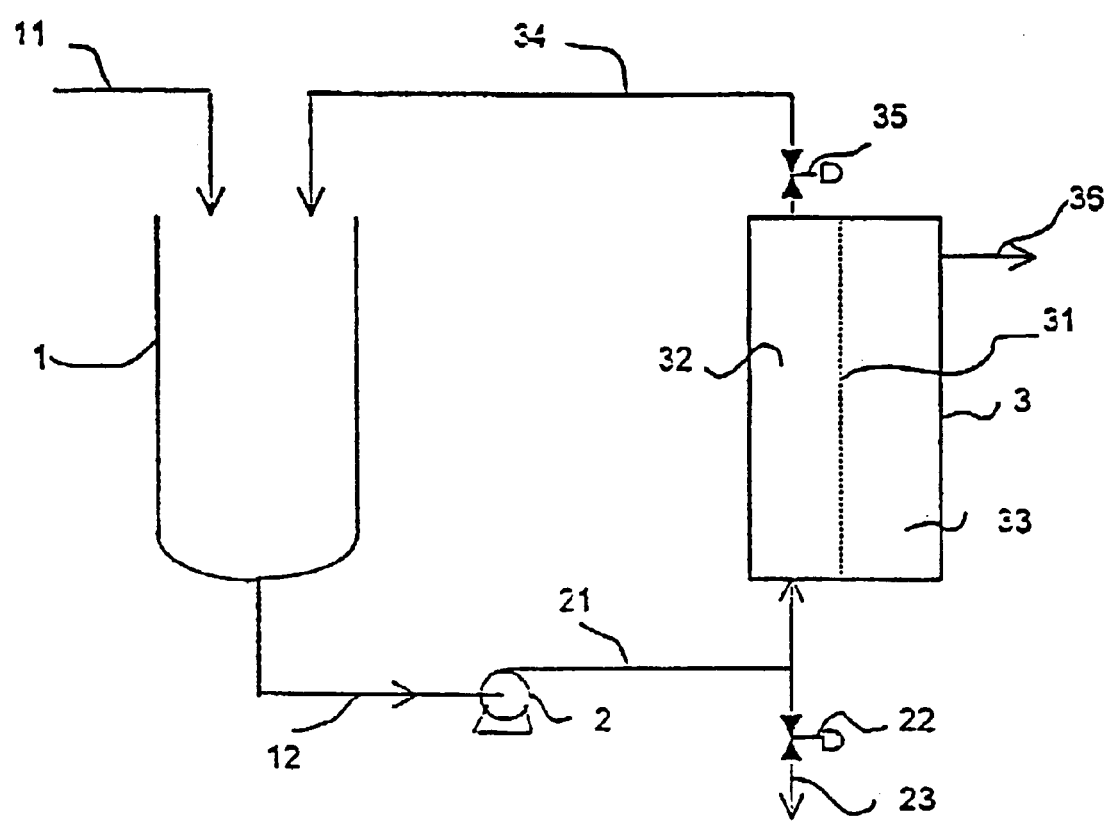
FIG. 1 shows an industrial application of the invention wherein a semicontinuous operating tangential filtration is used.

With reference to FIG. 1, an OAT suspension-containing feedstock is charged in vessel 1 through line 11. OAT suspension is kept homogeneous by means of any conventional stirring equipment not shown in the drawing. Through line 12 OAT suspension is aspirated by pump 2 and sent through line 21 to an end section of the filtration equipment 3.

The filtration equipment 3 is divided in two compartments: retentate compartment 32 and permeate compartment 33. The above compartments are separated by the filtrating surface 31.

Retentate, i.e. OAT suspension, enters continuously the compartment 32 through line 21 and tangentially strikes filtration surface 31 and exits from the opposite end of equipment 3 and then, by means of line 4 returns to suspension vessel 1.

Pump 2 as well as the associate control valve 35 assures that the desired pressure and tangential speed is maintained in the compartment 32 of equipment 3 during all operation time. Permeate compartment 33 operates under a pressure lower than the one of retentate compartment 32, allowing permeate to pass through filtration surface 31 in an amount depending on the pressure difference between compartments 32 and 33. Permeate continuously exits from equipment 3 through line 36 and is recycled to the melamine process.

Once the desired retentate concentration increase is reached (typically 16 times, but it may also reach up to 24 times the starting concentration), retentate is discharged through valve 22 into line 23 to be sent to solid (OAT) recovering section.

Figure 2:
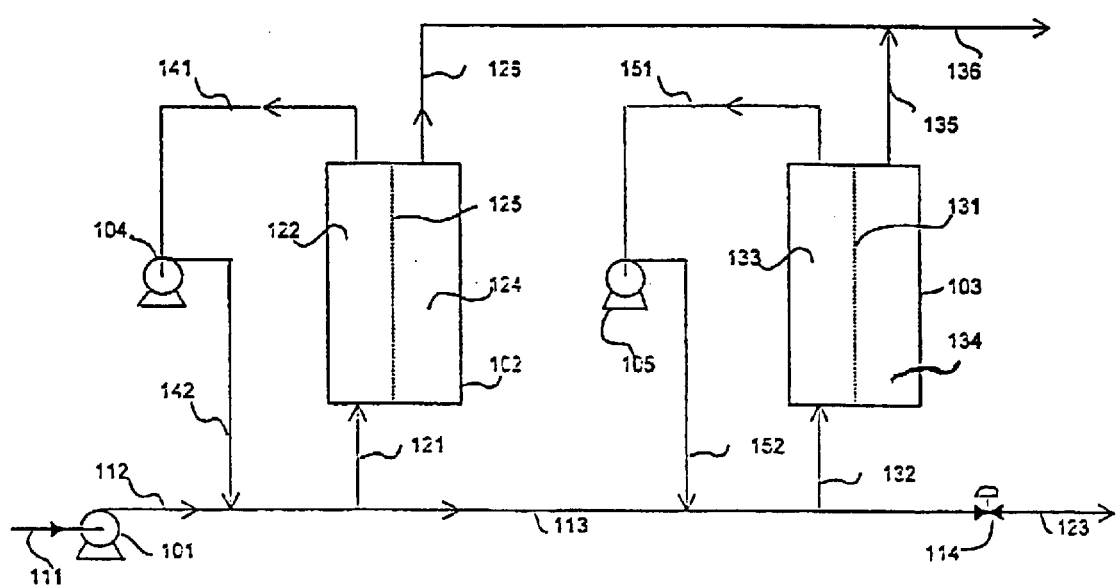
FIG. 2 shows a continuous operating tangential filtration scheme.

With reference to FIG. 2, the invention treatment process will be now described in its continuous operating mode.

In order to simplify the description a two-stage cascade process will be taken in consideration. However the stage number may be more than two. The optimum number of stage depends on economy evaluations.

In fact, increasing the number of stages will require an increase of plant complexity and consequently the number of necessary apparatuses while a reduction of filtrating surface can be used to reach the same results.

Pump 101 draws OAT suspension from a reservoir (not shown in the drawing), through line 111 and forces the suspension, through line 112, in the filtration system consisting of two stages in cascade, composed of the recycle pump 104 together with the filtration device 102 and the recycle pump 105 together with the filtration device 103.

OAT suspension, by means of line 121 enters the retentate circuit of the filter 102 composed of the recycle pump 104, the delivery line 142, the inlet line 121, the retentate compartment 122, (located inside the filter 102) and the outlet line 141 communicating with the pump 104. An OAT suspension characterised by having a solid concentration which is intermediate between the inlet and the outlet suspension flows in continuous in the retentate circuit. Pump 104 guarantees the desired tangential speed of retentate over the filtrating surface 125 inside the filter 102. Retentate pressure within compartment 122 is assured by the pump 101 and the counter-pressure valve 114 located at the exit of the two stage filtering system. Owing to the fact that pressure in the permeate compartment 124 is kept at a value lower than the one of compartment 122, a continuous passage of clear solution through the filtrating surface 125 is established; such clear solution is recovered in compartment 124 and then exits through line 126.

Since the pump 101 flow rate is designed at a value higher than the amount of permeate passing through the filtration surface 125, the excess fluid passes through line 113 to subsequent filtration step, more particularly enters the relevant retentate circuit consisting of recycle pump 105, delivery line 152, inlet line 132, retentate compartment 133, (located inside the filter 103), and line 151 which returns the retentate back to pump 105. Also in this circuit the retentate circulates continuously and its solid concentration is the final predetermined one. OAT containing retentate is extracted through line 123; the retentate concentration is 16 to 24 or more times the OAT concentration of the feedstock entering through line 112.

In this second filtration step, tangential speed on the filtration surface 131 is kept to desired value by means of the circulation pump 105. The connection between the above two filtration stages, allows to maintain in the retentate compartment 133 of the filter 103 practically the same pressure as in the retentate compartment 122 of the filter 102, while the permeate compartment 134 of the filter 103 is kept under the same pressure as the corresponding compartment 124 of the filter 102 because of the connection between lines 135 and 126.

Permeates coming out from the compartments 124 and 134 combine themselves by means of lines 126 and 135. Thereafter they exit from the system trough the line 136 into a recovering reservoir not shown in the drawing, wherefrom are recycled to process.

Permeate flow coming out of 136 is at least 94%, in practice more than 96% of the suspension inlet flow entering 111. Permeate, deprived of almost all OAT can be totally recycled to the melamine process.

Figure 3:
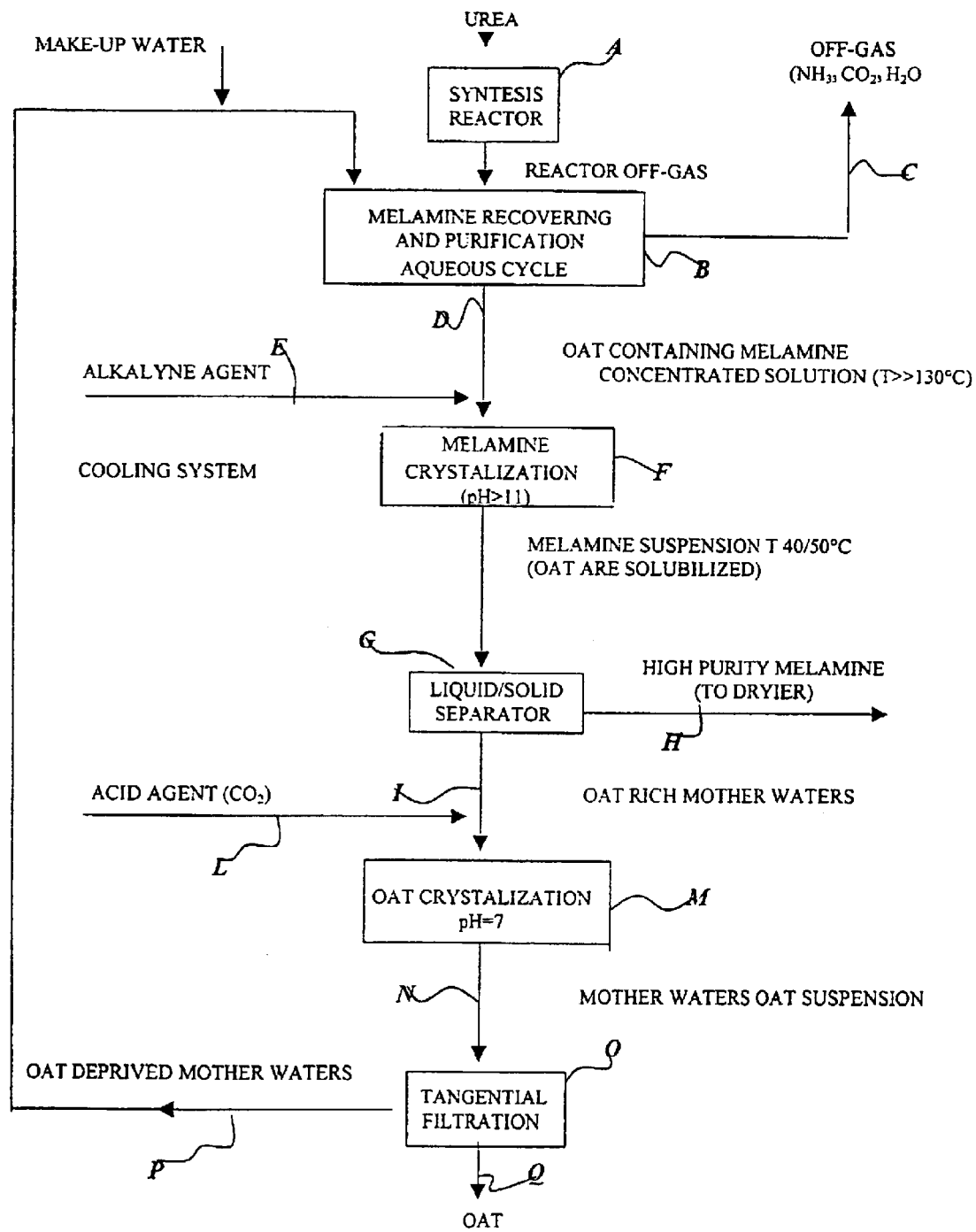
FIG. 3 is a block diagram showing where OAT suspension tangential filtration is located in the melamine manufacturing process.

In FIG. 3, it is shown, in form of block diagram, a melamine synthesis process in which the invention water treatment process is inserted.

Urea is transformed into melamine at high conversion in the synthesis reactor A. All reactor effluent enters the melamine aqueous recovery and purification circuit B, wherein gas by-products, consisting of ammonia and carbon dioxide are separated and sent out of the unit as water sturated gases (off-gas) through line C:

Said off-gas coming out of line C are usually recovered by returning back to urea synthesis plant.

From the purification circuit comes out, through line D a melamine containing liquid stream, at a temperature higher than 130° C. Said stream contains also OAT, as impurities to be removed. For this reasons through line E, an alkaline agent is added thereto in order to increase the pH up to a value grater than 11 and the solution is sent to in a crystallisation vessel F where the temperature is lowered to 40/50° C. In these conditions melamine only precipitates and is collected at high purity in the separator G. The high purity melamine is sent to drying section through line H.

Because of the high pH value, OAT remain in solution. OAT-rich mother liquor coming out of liquid—solid separator G, are additioned of an acidifying agent (preferably $CO_2$) trough line L in order to lower the pH to 7. Under this condition OAT are practically insoluble and then precipitate in form of a very diluted suspension of milky appearance in the crystallising vessel M.

The suspension is transferred through line N to the tangential filtration system O, which separates the almost total solvent (94 to 96 and more percent) which contains as a solution the amount of melamine corresponding to saturation at 40/50° C. (about 0.7 to 1% wt.) and a negligible amount of OAT (less than 100 ppm).

The above stream is totally recycled, through line P to melamine collecting and purifying circuit B, enabling the complete recovery of its melamine content.

On the other hand OAT are collected as retentate in form of a solid rich suspension and sent through line Q to a conventional recovery section, not shown on the drawing. OAT content in the stream Q is 16 to more than 24 times the content of the stream fed through line N to the tangential filtering unit O.

EXAMPLE 1

10 litres of mother liquor resulting from the melamine crystallisation and separation whose pH is reduced to 7 by $CO_2$ addition are fed to a system as the one shown in FIG. 1.

The $CO_2$-treated mother liquor has a milky appearance and contains about 40 g of OAT (4000 ppm) practically all in suspension.

The filtering surface consists of a 750 mm long hollow cylindrical candle filter, whose external and internal diameters are 10 mm and 7 mm, respectively. The candle filter is made of alumina having an average porosity of 50 nanometers. The above said suspension is circulated inside the cylindrical candle with an average flow rate of 4.5 m/s. Pressure in the retentate side is kept at a constant value of 2.5 bars for the entire period of time of the test. Permeate is recovered directly into a proper container kept under atmospheric pressure.

An rapid reduction of permeate flow-rate is experienced in the first 100 minutes of circulation, then the flow rate stabilishes at about 150–160 liters/hm² until the end of the test.

Permeate collected during the whole filtration period was clear.

The test was interrupted after 3 hours of continuos operation due to failure of pump priming because of small amount of circulating retentate.

9.42 litres of clear permeate was collected whose chemical analysis showed a content of 0.91 melamine and 87 ppm of OAT. The increase of solid OAT concentration in the retentate was 17.2 times the original concentration.

EXAMPLE 2

A system according to FIG. 1 but of bigger size than the one used in previous example, was loaded with 150 litres of the same mother liquors suspension as in example 1, at a temperature of 50° C. and a pH 7. The suspension contained 570 g of OAT practically all as suspension and 1400 g of melamine all of them as a solution.

As a filtrating surface, was used an industrial filtering element made of the same material as the candle of example 1, consisting of a hexagonal section parallelepiped 1020 mm long and 28 mm thick. Inside the parallelepiped 19 channels having 4 mm internal diameter are provided according to an hexagonal concentric configuration consisting of a central channel surrounded by six channels located at the vertices of a hexagon which is on its turn surrounded by twelve equidistant channels according to a second hexagonal pattern.

The channels are parallel to the parallelepiped axis.

The overall channel internal surface is 0.24 m$^2$.

The suspension circulates inside the 19 channels at a speed of 4.3 m/s.

The differential pressure through the filtering surface was kept constant at a value of $2.5 \times 10^5$ Pa, as in example 1.

Also in this example, after the initial two hours, the retentate flow stabilishes, with a slight reduction, to a value of 145 to 150 liters/h.m$^2$.

During a period of 4 hours a perfectly clear permeate was collected. After 4 hours and 3 minutes a very slight opalescent permeate was observed and the run was discontinued. The opalescent permeate, obtained during the last three minutes of the test was not taken in consideration, only clear permeate collected during the first 4 hours was evaluated. Total collected permeate was 144.8 litres. Opalescent permeate corresponding to the last three minutes of the test was added to retentate amounting to 5.2 litres with 602 g of solid content (measured after water evaporation). Collected permeate amounted to 96.5% of the initial suspension and the amount of OAT in the permeate was 92 ppm.

The total amount of solids in retentate was 115.8 g/l., 110 g/l of which are suspended solids. Owing to fact that suspension initial solid dispersion content was 570/150=3.8 g/l, the retentate suspended solid content increase resulted of 29 times.

What is claimed is:

1. A process to recover bosh melamine and oxyaminotriazines (OAT) from the mother liquor of melamine crystallization comprising the following steps:
   a) adding an alkaline agent to a melamine and OAT containing aqueous solution at high temperature until a pH of a resulting solution reaches a value of at least approximately 11;
   b) crystallizing at least a portion of the melamine to obtain precipitated melamine by cooling the resulting solution;
   c) separating and recovering the precipitated melamine from the mother liquor;
   d) acidifying the mother liquor with a suitable acid to reach a pH of approximately 7 resulting in precipitation of the OAT to obtain a suspension;
   e) filtering the suspension using tangential filtration to obtain a permeate containing all of the melamine not precipitated in step b) and a retentate comprising an OAT dispersion having an OAT concentration at least fifteen times an original OAT concentration;
   f) recycling the permeate to recover an amount of melamine not precipitated in step b); and
   g) recovering OAT from the retentate.

2. The process to recover both melamine and oxyaminotriazines (OAT) from the mother liquor of melamine crystallization according to claim 1 wherein the alkaline agent solution treatment of stage a) takes place at a temperature higher than approximately 130° C.

3. The process to recover both melamine and oxyaminotriazines (OAT) from the mother liquor of melamine crystallization according to claim 1 wherein the melamine is crystallized in step b) by cooling the solution to a temperature in the range of approximately 40° to 50° C.

4. The process to recover both melamine and oxyaminotriazines (OAT) from the mother liquor of melamine crystallization according to claim 1 wherein the pH in step d) is between approximately 6.5 and 7.5.

5. The process to recover both melamine and oxyaminotriazines (OAT) from the mother liquor of melamine crystallization according to claim 1 wherein a surface filtering material is used for tangential filtration and is resistant to pressure and chemical agents.

6. The process to recover both melamine and oxyaminotriazines (OAT) from the mother liquor of melamine crystallization according to claim 1 wherein a surface filtering material is used for tangential filtration and is selected from among alumina, silico-alumina, zirconia, titania, boria, zeolites, thoria and mixtures thereof.

7. The process to recover both melamine and oxyaminotriazines (OAT) from the mother liquor of melamine crystallization according to claim 6 wherein the surface filtering material used for tangential filtration according step e) comprises a high purity alumina.

8. The process to recover both melamine and oxyaminotriazines (OAT) from the mother liquor of melamine crystallization according to claim 1 wherein a surface filtering material is used for tangential filtration and exhibits a porosity lower than 5 micron.

9. The process to recover both melamine and oxyaminotriazines (OAT) from the mother liquor of melamine crystallization according to claim 8 wherein the surface filtering material used for tangential filtration exhibits a porosity lower than 0.2 micron.

10. The process to recover both melamine and oxyaminotriazines (OAT) from the mother liquor of melamine crystallization according to claim 8 wherein the surface filtering material used for tangential filtration exhibits a porosity in the range of 20 to 100 nanometers.

11. A process to recover both melamine and oxyaminotriazines (OAT) from the mother liquor of melamine crystallization comprising the following steps:
   a) adding an alkaline agent to a melamine and OAT containing aqueous solution at high temperature until a pH of a resulting solution reaches a value of at least approximately 11;
   b) crystallizing at least a portion of the melamine to obtain precipitated melamine by cooling the resulting solution;
   c) separating and recovering the precipitated melamine from the mother liquor;
   d) acidifying the resulting solution to reach a pH of about 7 resulting in precipitation of the OAT to obtain a suspension;

e) filtering the suspension using tangential filtration to obtain a permeate containing all of the melamine not precipitated in step b), and a retentate comprising an OAT dispersion having an OAT concentration at least fifteen times an original OAT concentration;

f) recycling the permeate to recover an amount of melamine not precipitated in step b); and g) recovering OAT from the retentate.

12. The process to recover both melamine and oxyaminotriazines (OAT) from the mother liquor of melamine crystallization according to claim 11 wherein the melamine is crystallized in step b) by cooling the solution to a temperature in the range of approximately 40° to 50° C.

13. The process to recover both melamine and oxyaminotriazines (OAT) from the mother liquor of melamine crystallization according to claim 12 wherein the pH in step d) is between approximately 6.5 and 7.5.

14. The process to recover both melamine and oxyaminotriazines (OAT) from the mother liquor of melamine crystallization according to claim 13 wherein a surface filtering material is used for tangential filtration and is resistant to pressure and chemical agents.

15. The process to recover both melamine and oxyaminotriazines (OAT) from the mother liquor of melamine crystallization according to claim 14 wherein a surface filtering material is used for tangential filtration and is selected from among alumina, silico-alumina, zirconia, titania, boria, zeolites, thoria and mixtures thereof.

16. The process to recover both melamine and oxyaminotriazines (OAT) from the mother liquor of melamine crystallization according to claim 15 wherein the surface filtering material used for tangential filtration according step e) comprises a high purity alumina.

17. In a process to recover both melamine and oxyaminotriazines (OAT) from the mother liquor of melamine crystallization comprising the following steps:

a) adding an alkaline agent to a melamine and OAT containing aqueous solution at high temperature until a pH of a resulting solution reaches a value of at least approximately 11;

b) crystallizing at least a portion of the melamine to obtain precipitated melamine by cooling the resulting solution;

c) separating and recovering the precipitated melamine from the mother liquor;

d) acidifying the mother liquor with a suitable acid to reach a pH of approximately 7 resulting in precipitation of the OAT to obtain a suspension;

e) separating the suspension obtained in d) to obtain a permeate comprising as a solution all of the melamine not precipitated in step b) and a retentate comprising an OAT in form of a colloidal precipitate; and f) recovering OAT from the retentate, the improvement comprising:

using a tangential filtration, as a separation technology according to step e), resulting in an OAT concentration in the retentate being maintained at a value of at least fifteen times an original OAT concentration.

* * * * *